(12) United States Patent
Horhota et al.

(10) Patent No.: US 6,294,194 B1
(45) Date of Patent: Sep. 25, 2001

(54) METHOD FOR EXTRACTION AND REACTION USING SUPERCRITICAL FLUIDS

(75) Inventors: Stephen T. Horhota, Brookfield; Said Saim, New Milford, both of CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 0 days.

(21) Appl. No.: 09/517,883

(22) Filed: Mar. 3, 2000

Related U.S. Application Data (63) Continuation-in-part of application No. 09/157,267, filed on Sep. 21, 1998, now Pat. No. 6,228,394.
(60) Provisional application No. 60/062,099, filed on Oct. 14, 1997.

(51) Int. Cl.$^7$ ............................. A61K 9/64; A61K 9/48; F26B 3/00

(52) U.S. Cl. ........................... 424/456; 424/451; 34/329; 34/337; 34/341

(58) Field of Search .................................. 424/456, 451; 34/329, 337, 341

(56) References Cited

U.S. PATENT DOCUMENTS

| | | |
|---|---|---|
| 3,594,983 | 7/1971 | Yearout . |
| 3,806,619 | 4/1974 | Zosel . |
| 4,059,308 | 11/1977 | Pearson et al. . |

(List continued on next page.)

FOREIGN PATENT DOCUMENTS

| | | |
|---|---|---|
| WO 99/18939 | 4/1999 | (WO) . |
| WO 99 49996 | 10/1999 | (WO) . |

OTHER PUBLICATIONS

Hannay, et al, "On the Solubility of Solids in Gases", Royal Society of London Proceedings, London, vol. 29, p. 324 (1879).

Tiltsher, et al,"A Mild and Effective Method for the Reactivation or Maintenance of the Activity of Heterogeneous Catalysts", Angew. Chem. Int. Ed. Engl. 20:892, 1981.

Larson, et al, "Evaluation of Supercritical Fluid Extraction in the Pharmaceutical Industry", Biotechnology, Progress, vol. 2, No. 2, 1986, pp. 73–82.

McHugh, et al, Supercritical Fluid Extraction, Principles and Practice, 2nd Ed., Butterworth–Heinemann, 1994, p. 369, p. 191.

Donsi, et al, "Micronization by Means of Supercritical Fluids: Possibility of Application to Pharmaceutical Field", Pharm. Acta helv. 66, Nr. 5–6 (1991), P 170–173.

Francis, A. W.., "Ternary Systems of Liquid Carbon Dioxide", J. Phys. Chem., 1954, 58, 1099.

Gallagher, et al, "Gas Anitsolvent recrystallization: New Process to Recrystallize Compounds Insoluble in Supercritical Fluids", 1989 Am. Chem. Soc., Ch. 22, pp. 334–354.

Yeo, et al, "Formation of Microparticulate Protein Powders Using a Supercritical Fluid Antisolvent", Biotechnology and Bioengineering, Vo. 41, pp. 341–346, 1993.

(List continued on next page.)

Primary Examiner—Thurman K. Page
Assistant Examiner—Brian K. Seidleck
(74) Attorney, Agent, or Firm—Robert P. Raymond; Alan R. Stempel; Mary-Ellen M. Devlin (57) ABSTRACT

Methods for removing soluble material from confined spaces within substrates such as containers, capsules and porous powders comprising extraction with supercritical fluids, the pressure of which is preferably modulated between an upper level and a lower level within a relatively narrow range of fluid pressure and density. The method permits enhanced extraction efficiency, catalytic reaction rates and ability to maintain catalyst activity.

26 Claims, 3 Drawing Sheets

U.S. PATENT DOCUMENTS

| | | |
|---|---|---|
| 4,061,566 | 12/1977 | Modell . |
| 4,163,580 | 8/1979 | Pearson et al. . |
| 4,338,199 | 7/1982 | Modell . |
| 4,721,826 | 1/1988 | Tiltscher et al. . |
| 4,970,093 | 11/1990 | Sievers et al. . |
| 5,267,455 | 12/1993 | Dewees et al. . |
| 5,287,632 | 2/1994 | Heit et al. . |
| 5,360,478 | 11/1994 | Krukonis et al. . |
| 5,389,263 | 2/1995 | Gallagher et al. . |
| 5,514,220 | 5/1996 | Wetmore et al. . |
| 5,599,381 | 2/1997 | Whitlock et al. . |
| 5,641,510 | 6/1997 | Clark et al. . |
| 5,725,756 | 3/1998 | Subramaniam et al. . |
| 5,833,891 | 11/1998 | Subramaniam et al. . |

OTHER PUBLICATIONS

Tom, et ali, "Particle Formation with Supercritical Fluids—A Review", J. Aerosol Sci., vol. 22, No. 5, pp. 555–584, 1991.

Mohamed, et al, "Effects of Process Conditions on Crystals Obtained from Supercritical Mixtures", AIChE Journal, vol. 35, No. 2, 1989, pp. 325–328.

Fig. 1

(1) 14 BAR PRESSURE MODULATION WITH 40 S PERIOD
(2) 97 BAR PRESSURE SWING WITH 15 MIN PERIOD
(3) 14 BAR PRESSURE MODULATION WITH 4 S PERIOD
(4) 0.7 BAR PRESSURE MODULATION WITH 4 S PERIOD
(5) CONVENTIONAL SFE AT NEARLY CONSTANT PRESSURE

METHOD FOR EXTRACTION AND REACTION USING SUPERCRITICAL FLUIDS

This application is a continuation-in-part of patent application Ser. No. 09/157,267, filed Sep. 21, 1998, now U.S. Pat. No. 6,228,394 B1, which claims, as does the present application, priority to provisional application Ser. No. 60/062,099, filed Oct. 14, 1997, the disclosures of both which are incorporated by reference in their entirety.

BACKGROUND OF THE INVENTION

1. Field of the Invention

The present invention relates to a method for improving mass transfer rates into dense fluids and, in particular, supercritical fluids. More particularly, the present invention is directed to a method for removing soluble compositions from materials. The present invention finds application in the removal of manufacture residues such as capsule mold lubricants, in the extraction of desirable material, residual solvents, and contaminants from chemical and pharmaceutical containers and preparations, and in promoting the transfer of reaction products and by-products from catalyst pores to a bulk phase thereby maintaining the activity of the catalyst and improving reaction rates.

2. Background of the Related Art

Extraction procedures are used to transfer solutes from a solid or liquid phase to a gaseous, liquid or supercritical phase. Extensive use is made of solvent extraction in industry. However, it is well known in the art that solvent extraction suffers from a number of drawbacks including environmental and health concerns associated with many solvents, residual contamination of the treated material with the solvent itself, as well as intensive/high costs often associated with conventional extraction-distillation schemes.

Extraction procedures using supercritical fluids (SCFs) rather than organic solvents have been growing in popularity. A fluid whose temperature and pressure are simultaneously higher than its critical temperature and pressure is supercritical. The surprising solubility of solids in SCFs was first noted in the late 1800's (Hannay and Hogarth, Proc. Roy. Soc., London A29, 324 (1879)). Actual solubility of non-volatile solutes in SCFs may be as much as $10^6$ times higher than would be calculated assuming ideal gas behavior at the same temperature and pressure.

The most ubiquitous SCF, carbon dioxide ($CO_2$, $T_c$=304.1 K, $P_c$=73.8 bar), is a gas at ambient conditions. In a supercritical state, it is essentially a compressed, high density fluid at mild temperature. It is relatively innocuous, inexpensive and non-reactive under most operating conditions. Other SCFs may have higher $T_c$ and $P_c$ and may not be innocuous. Contrary to liquids, the density, solvent power or selectivity of a SCF can be easily altered with relatively small changes in pressure or by addition of small amounts of an organic solvent. The change in $CO_2$ density (with pressure at 35° C. determined using an equation of state developed specifically for $CO_2$) does not increase linearly with increasing pressure. Small changes in pressure can produce large changes in density when operating close to the critical point, for instance at 83 bar where the compressibility of $CO_2$ is high. Relatively large changes in pressure may result in in relatively small changes in density when operating at higher pressures, for instance at 700 bar where $CO_2$ compressibility is low.

Because of its gaseous nature, a SCF is also characterized by a higher diffusivity and lower interfacial tension than liquids, and has the ability to freely penetrate a matrix such as pores in a catalyst with no phase change. A SCF such as $CO_2$ can also be vented out of an extractor, leaving no residue and no need for drying.

Numerous gases other than $CO_2$ may be converted to SCFs at temperatures and pressures commonly employed in industry, including, without limitation, hydrocarbons (e.g. methane, ethane, propane, butane, pentane, hexane, ethylene and propylene), halogenated hydrocarbons, and inorganic compounds (e.g., ammonia, carbon dioxide, sulfur hexafluoride, hydrogen chloride, hydrogen sulfide, nitrous oxide and sulfur dioxide). SCFs have been used to extract numerous compounds including aliphatic and aromatic hydrocarbons, organic esters of inorganic acids, organosilicons and organometallics.

SCFs have found a particular niche in cleaning items. U.S. Pat. No. 5,267,455, incorporated by reference herein, discusses a number of references which disclose the use of SCFs to remove materials as diverse as oil and carbon tetrachloride residues from metals to soils from garments. SCFs have also been used as extracting agents to deasphalt lubricating oils, to obtain edible oils, and decaffeinate coffee (Zosel, U.S. Pat. No. 3,806,619).

SCFs have been reported to be useful in other extraction applications including re-dissolution of adsorbed material (U.S. Pat. No. 4,061,566), the formation of porous polymers, removal of residual solvents from articles formed by compression such as tablets (U.S. Pat. No. 5,287,632), monomer purification and fractionation of various polymers. A possible drawback of SCFs such as $CO_2$ is that they generally have limited solvent power for many polar and high molecular weight compounds. Therefore, they are often used for material purification or selective extraction.

SCFs are also used for crystallization (See, e.g., U.S. Pat. Nos. 5,360,478 and 5,389,263) as well as micronization of solutes in organic solutions (See, e.g., U.S. Pat. No. 5,833,891). Solutes may also be micronized by rapidly expanding a SCF solution down to a pressure where the solute is no longer soluble.

Use of SCFs as reaction media includes applications for chemical deposition of a reaction product on substrates (See, e.g., U.S. Pat. No. 4,970,093), oxidation of organics in water (Modell, U.S. Pat. No. 4,338,199), and maintenance of catalyst activity (U.S. Pat. Nos. 4,721,826 and 5,725,756). For example, Tiltsher et al. (Angew. Chem. Int. Ed. Engl. 20:892, 1981) report that the activity of a porous catalyst can be restored by elevating pressure or temperature to a level where the deposited coking compounds are re-dissolved in a supercritical reaction mixture. However, on a whole, catalyst reactivation and deactivation using SCFs has yet to become adopted widely in the industry possibly due to either low catalyst activity when compared to the alternate industrial processes in place, or because catalyst activity is not maintained at a reasonably high level for long enough time. Applicants have hypothesized that diffusion limitations of reactants, products, and catalyst deactivating material are still present, thereby limiting the usefulness of these techniques.

A substantial discussion of the many uses to which SCFs have been employed is set forth in the text *Supercritical Fluid Extraction* by Mark McHugh and Val Krukonis (Butterworth-Heinmann 1994).

While SCFs proffer many advantages over organic solvents, several investigators have noted drawbacks with conventional supercritical fluid extraction (SFE) procedures. A problem associated with SCFs is the low mass transfer rate of a solute in a confined space to a bulk supercritical phase. The rate of solute extraction depends on the solute's dissolution rate, solubility, and rate of mass transfer into the bulk solvent phase. Despite higher diffusivity than liquids, SCFs still exhibit limited ability to rapidly transfer extracted material from confined spaces to a bulk supercritical phase. Lack of thorough mixing between the fluid in the bulk phase and the fluid in the confined space limits mass transfer to essentially the diffusion rate of the solute(s). Normally, dissolution and mass transfer rates can be enhanced by thorough mixing between a bulk phase and a solute phase as by means of an impeller; however, the degree of enhancement in mass transfer rates is limited when the solute resides in confined spaces such as micropores, interstices, nearly closed containers or closed containers where little mixing will take place. In these cases, interphase mass transfer between the fluid in the confined spaces and the fluid in the bulk phase is often a rate limiting step.

A variety of applications in the pharmaceutical, chemical and other industries suffer from problems associated with slow mixing between a fluid or fluid mixture in a confined solid space, and a fluid or fluid mixture in a bulk phase. These problems can be so severe that they can reduce the efficiency of the process, sensibly increase processing costs, or require the use of alternative, less environmentally friendly processes to overcome these limitations.

A particular problem identified in the pharmaceutical arts is the presence of soluble impurities in drug substances and delivery formulations. For example, residual amounts of organic solvents and lubricants used in formulation processes are frequently found in porous matrix formulations. Such solvents may hamper dissolution rate by filling microchannels and by making active drug inaccessible to gastrointestinal fluids.

Soluble impurities may also be found in the drug active itself. Similarly, it is known that hard gelatin capsules used to store pharmaceutical powders which are to be administered to a patient by inhalation upon puncture of the capsule often provide non-uniform release of the pharmaceutical powder. It has recently been discovered that the non-uniform release is due to lubricant and/or plasticizer compositions which are deposited on the internal surfaces of capsules during the manufacture of the capsule (the lubricants being used to permit removal of the formed capsule shell from its molding pin-special plasticizers are sometimes used to improve capsule elasticity). One group has proposed that the capsules, conventionally sold as an assembled unit, be opened and exposed to a solvent which dissolves the lubricant to prevent sticking of the drug to the capsule interior (See, U.S. Pat. No. 5,641,510). Such technique, however, may suffer from a number of drawbacks including: the requirement that the two halves of the shell be separated when extracting and drying the capsules, possible residual organic solvent contamination, and the need for drying of the capsule shells after treatment with the solvent. Methods of extraction that allow for the removal of mold lubricant from assembled capsules, as provided by the manufacturer, are more desirable than methods requiring the capsules to be disassembled prior to their extraction; however, mass transfer of lubricant from inside the capsules to the bulk solvent through the tight space between the capsule cap and capsule body is limited when using conventional methods of extraction.

The inability to extract desirable material, residual solvents, or other soluble impurities from confined solid spaces can also pose significant problems in other areas of the chemical arts.

It is well known in the chemical arts that catalytic loss of activity occurs as catalytic reactions proceed. Loss of activity is generally associated with: (1) a reduction in the number of active sites on the internal or external surface of the catalyst due primarily to poisoning of the catalyst with compounds carried over into the reaction system; (2) aging caused by structural changes of the catalytically active surface (e.g. by sintering, recrystallization and the like); (3) deposition of sparingly volatile substances on the external or internal surface of the catalyst (so-called "coking") caused by either carry over into the reaction system or undesired parallel reactions or secondary reactions in the catalyst milieu. The primary methods used for reactivating catalysts are calcination and solvent extraction. Both of these methods, however, suffer from adverse effects; for example, calcination causes deactivation of the catalyst through aging, while solvent extraction introduces foreign substances into the reaction system. Coking of acid catalysts is particularly problematic (coking is typically caused by side reactions that involve mainly acid-catalyzed polymerization and cyclization of olefins that produce higher molecular weight polynuclear compounds which undergo extensive dehydrogenation, aromatization and further polymerization). Methods for efficiently and continuously removing catalyst coking material from catalyst pores would therefore be desirable.

An interdisciplinary problem is the problem of contamination found in the interstices of objects exhibiting porous surfaces, tight clearances, or which are otherwise swellable. Removal of contamination from interstices is difficult as the contaminant is protected from external cleaning agents (such as solvents, vacuum, etc.) by the interstice itself.

U.S. Pat. No. 5,514,220 to Wetmore et al. teaches that cleaning of porous materials and materials which exhibit tight clearances between adjoining components, such as gyroscopes, accelerometers, thermal switches, nuclear valve seals, electromechanical assemblies, polymer containers, special camera lenses, laser optics components and porous ceramics, can be improved by raising or spiking the pressure of the SCF to levels at least 103 bar greater than the initial pressure of the SCF. The large pressure pulses used by Wetmore et al. result in a relative difference between the uppermost and lowermost levels of density $$\% \ \Delta \rho = \left( \frac{\rho_{high} - \rho_{low}}{\rho_{high}} \right)_{Thigh} * 100$$

of the fluid in the range of 45% to 72%. This range is typical of those used in other pressure pulse or, alternatively pressure swing processes. Such large swings in fluid pressure and density are designed to purge a large fraction of the solute in solution out of the solid material and into the bulk phase within every period of pressure pulse. Few such pulses are therefore generally needed to complete an extraction process involving contaminants; however, such large drops in pressure can be accompanied by large drops in temperature, especially when using fluids such as $CO_2$ which can exhibit a relatively high Joule-Thompson coefficient. Contrary to processes such as conventional pressure swing adsorption (U.S. Pat. No. 3,594,983) which involve non-supercritical, low density gases where periodic and relatively large drops in pressure and density can be effected in a relatively short period of time, such drops cannot be easily achieved with SCFs. Because of the relatively much higher density of SCFs, purging of a large fraction of fluid out of the extraction vessel will normally require a longer time. Moreover, because of the higher Joule-Thompson coefficient of such fluids as $CO_2$, severe cooling and other processing problems will limit the ability to simultaneously rapidly drop pressure and rapidly reheat the vessel to processing temperature.

Another application of pressure pulse cleaning with SCFs is in polyethylene production where rapid, large pressure drops are used to strip off polyethylene deposited on heat transfer surfaces of the reactor (McHugh and Krukonis, 1994, p. 191)). Relatively large pressure swings are similarly used to re-dissolve adsorbed substances in SCFs (U.S. Pat. No. 5,599,381), and to extract minerals and hydrocarbons from cracks in subsurface deposits (U.S. Pat. Nos. 4,163,580 and 4,059,308).

Co-pending U.S. patent application No. 09/157,267, the international counterpart of which is published as WO 99/18939, a commonly assigned application, teaches that undesirable materials, in particular capsule mold lubricant, also can be removed from within the cavity delimited by the internal surfaces of gelatin capsules using SCFs even if the capsule shell counterparts are joined with one another to form one capsular element. In this patent application, methods for treatment of capsules used to store pharmaceutical formulations (referring to a formulation containing at least one active drug and, optionally, a pharmaceutically acceptable carrier or excipient) in capsules are described. Capsules may be manufactured from numerous materials including gelatin, cellulon and modified cellulose, starch and modified starches and plastic. The drug is delivered by dry powder inhalation devices, which pierce the capsules to allow the patient to inhale the drug. A SCF such as $CO_2$ has a special affinity for lipidic material such as lubricants used for capsule mold release, and is therefore particularly suitable for such an application. $CO_2$ also does not alter the color, appearance or physical properties of the capsules. Reduction in the amount of lubricant in the capsule is disclosed to reduce retention of drug product in the capsule and to improve the reproducibility of the amount of drug inhaled.

While large swings in pressure/density improve extraction, such swings have been found to result in processing problems. Large pressure/density swings often result in severe cooling of the SCF and extraction vessel. The cooling problem can be especially problematic with larger vessels, and particularly with use of fluids such as $CO_2$ which exhibit relatively high Joule-Thompson coefficients. Cooling may adversely affect endothermic reactions, produce non-uniformity in temperature within a vessel, and cause condensation or undesired precipitation of extracted material. Large pressure pulses may also induce substantial changes in fluid density, solvent power, temperature and reaction rates (reaction rates may be decreased either due to cooling or changes in SCF density). Repeated cooling and heating combined with repeated large pressure drops can lead to fatigue of the pressure vessel. As large pressure/density swings further typically require a long time to implement, catalyst deactivation may also occur. Moreover, when large pressure drops are used, extraction does not take place constantly at the pressure where solvent power is high, thereby reducing extraction efficiency.

For instance, adiabatic temperature drops for $CO_2$ can be estimated using published data for the Joule-Thompson coefficient $$\mu = \left(\frac{\delta T}{\delta P}\right)_H$$

where H is the enthalpy, T is the temperature and P is the pressure, provided in Perry's handbook [Perry and Green, Perry's Chemical Engineering Handbook, Sixth Ed., p. 3–109, 1984). It is found that at 50° C., a drop in pressure from 101 bar to levels resulting in a change in density $$\% \, \Delta\rho = \left(\frac{\rho_{high} - \rho_{low}}{\rho_{high}}\right)_{Thigh} * 100$$

of 60% results in a drop in temperature of 18.3° C. In this instance, the potential drop in temperature is relatively large and its may not be possible to rapidly reheat a high pressure vessel back to the temperature prevailing just prior to initiating pressure drop. Repeating such pressure swings as in pressure pulse and swing processes may eventually cause the vessel temperature to drop below the critical point and liquid $CO_2$ may then form.

The walls of large high pressure vessels are generally thick and made out of stainless steel. Because stainless steel exhibits low thermal conductivity, it is often not heated externally, and fluids are normally preheated to processing temperature prior to entering the vessel. A large temperature drop is therefore often difficult to overcome, and a large section of the vessel close to the exit or expansion valve can become excessively cold. Materials sensitive to large swings in temperature and/or pressure can thus be especially affected. Large pressure/density swings have been seen to lead to damage, degradation or collapse of materials sensitive to repeated large changes in temperature, pressure or fluid density. Even if the materials are not sensitive to large pressure and/or temperature swings, this creates regions of non-uniformity in the vessel temperature which can result in non-uniformity in the fluid solvent power. The treated material may thus not be uniformly depleted of its soluble material, and the extraction efficiency will be non-uniform. Material containing liquid substances such as water or other polar material that freezes in the cooled region could also block access to soluble material.

Even in the absence of a temperature drop, a large change in density can have negative effects. For instance, at 40° C., the solubility of benzoic acid drops from about 0.45% to 0.009% as the density of $CO_2$ is reduced 60%, from 0.75 g/mL to 0.3 g/mL (McHugh and Krukonis, p.369). Such a large drop in solubility can cause the dissolved solute to precipitate.

Use of large pressure and density swings for maintenance of catalytic activity is not possible because large changes in fluid density as means of purging coking compounds could not take place fast enough to respond to the need to rapidly purge by-product material out of a catalyst matrix before it undergoes transformation into undesirable, insoluble material. Such changes could also induce large, undesirable variability in reactions rates and selectivities.

The above examples suggest that the pressure swing and pressure pulse processes, which were originally developed for non-SCF applications, are generally not suitable for applications involving fluids such as $CO_2$, which is the SCF of choice. Prior art applications involving non-SCFs such as pressure swing adsorption could not use a pressure modulation technique with relatively small pressure and density changes because those applications required relatively large pressure and density changes to be effective.

There is a need, therefore, for a process that improves interphase mass transfer between fluids in confined spaces and SCFs in a bulk phase so as to permit efficient extraction of contaminants found in such confined places without the limitations of previous art. Preferably such extraction should take place with relatively little change in the SCF density; little cooling of the vessel; no significant change in reaction rates; little if any precipitation of extract, reactants or products; no significant shattering, collapsing or degradation of sensitive material; and minimal, if any, fatigue on the pressure vessel in which extraction is conducted. Preferably the process would operate continuously near the highest pressure where the SCF solvent power and the solute concentration in the SCF can be at their highest.

SUMMARY OF THE INVENTION

The present invention provides a process by which material inside a confined space can be solubilized and efficiently transferred to a bulk fluid phase by employing SCF solvents in an original and judicious way. The process employs repeated modulation of SCF pressure/density between an upper level and a lower level within a relatively narrow range of fluid density, coupled with an adequate frequency of modulation to remove materials. The present method permits enhanced extraction rates and improved control of the rate of removal of materials into the extracting fluid without the limitations of the previous art. Surprisingly, it is found that the present method can be more than 7-fold more efficient than conventional SFE at extracting material such as solvents or polymers from confined spaces such as closed bottles which were previously not amenable to extraction by conventional methods. More surprisingly, the method is found to be efficient at extracting material in relatively large quantities and can therefore also be used in applications involving not only extraction of contaminants as in cleaning applications but also in extraction of bulk quantities of soluble material. This is demonstrated by the novel application of SCFs to the extraction of bulk material from such substrates as containers such as bottles, drums and syringes, which are to a large extent impervious to extraction with SCFs at constant pressure and were previously not addressed by other extraction techniques such as pressure pulse and pressure swing processes. According to this invention, such material is preferably extracted using relatively small modulations in fluid pressure and density. Such unique applications in addition to the applications to catalytic reaction enhancement open broad avenues for expanding the use of SCFs.

The effectiveness of relatively small magnitude pressure modulation in enhancing mass transfer was not envisioned by previous investigators partly because it was unobvious that relatively small but repeated changes in fluid density can have appreciable effects on mass transfer. Surprisingly our experimental and modeling studies have now demonstrated that pressure modulation can be even more efficient than pressure pulse and pressure swing extraction in removing soluble material from matrices without incurring the multitude of limitations associated with the prior art. Moreover, while pressure pulse and pressure swing processes have not been reported to be of any use in enhancing catalytic reaction rates and continuous maintenance of catalyst activity, the present invention is uniquely suited for such applications.

While not wishing to be bound by any theory, it is hypothesized that the enhancements and improvements provided by the present process result from an improved convective flow of the extracted material out of the matrix every time pressure is reduced, and improved convective flow of SCF containing less solute material every time pressure is increased. Such repeated convective flow can cause mixing and turbulence within the SCF in the confined matrix, and thereby increase the rate of extraction of the material from the substrate. High frequency modulations can also possibly cause propagation of mixing effects within the confined matrix thereby also increasing the extraction efficiency. It is therefore believed that it is possible to sensibly affect the rate of extraction of compounds dissolved in a SCF phase present inside a confined matrix by effecting convective flow into and out of the matrix rather than by relying solely on mostly slow diffusive flow as a means for transfer of solute from the SCF in the matrix to the bulk SCF phase.

It has been determined that substantial convective flow can occur using relatively small pressure modulations at relatively high frequencies correlating with relatively small changes in fluid density, where the physical properties of the fluid and vessel are little affected throughout the pressure modulation phase. Taking advantage of the gas-like compressibility and diffusivity, and liquid-like solvent power of SCFs, there is provided by the present invention a means to force a bulk SCF phase into confined spaces using a relatively small pressure increase and to force a small fraction of the content of confined spaces into the bulk phase using a relatively small pressure reduction. Repeated pressure modulation provides a means to repeatedly mix the content of the solute poor bulk phase and the solute rich confined phase, thereby enhancing extraction efficiency.

It has been found that the use of relatively small pressure/density modulations at relatively higher frequency allows more flexibility in processing and can yield high extraction efficiencies without incurring the multitude of problems associated with large swings in pressure. A high extraction efficiency of extraction can be achieved through control of the magnitude and frequency of relatively small changes in pressure/density. By use of the present invention, it is possible to achieve the same or even better extraction efficiency than possible with large pressure pulses. The present invention can be extended to reaction systems involving porous catalysts. When applied to reaction systems, it is possible to overcome a variety of problems associated with catalyst coking and inadequate reaction rates.

The magnitude of modulation in fluid density determines the magnitude of fluctuations in fluid solvent power and physical properties, reaction rates and adiabatic cooling effects. Contrary to previous art, in this invention the density and physical properties of the processing fluid do not experience considerable changes during pressure modulation. The driving force for mass transfer in this invention is relatively small changes in density. Contrary to pressure pulse or pressure cleaning, the change in fluid density is always kept relatively small, and the amount of fluid removed from the matrix is therefore relatively small within any period of pressure modulation. Because changes in density are relatively small when compared to prior art, they can be effected with a relatively higher frequency and always near the uppermost density where the solvent power is highest. The ability to control and increase the frequency of density modulation can provide an opportunity to be possibly even more effective at extracting soluble material from an insoluble matrix than possible with pressure swing and pressure pulse processes.

It has been determined that pressure modulations imparting relative differences in fluid density between the uppermost level of density and the lowermost level of density of no more than about 5% can be sufficient to effect a large enhancement in extraction efficiency when compared to conventional SFE at substantially constant pressure. Depending on the characteristics of the fluid, solute, matrix to be extracted, system and process under consideration, differences in density of up to 30% can be used. A 30% relative density difference is equivalent to a fluctuation in fluid density of about ±15% around the average fluid density and solvent powder. It is well below relative differences routinely used in the prior art and can therefore be used with much less effect on fluid properties. For instance, it is found that at 50° C., a drop in pressure from 101 bar to levels resulting in a relative difference in density of 5% and 30% respectively will result in adiabatic temperature drops of only 0.9° C. and 6.8° C. respectively. This compares to a drop of 18.3° C. when using a change in density of 60%. The present invention is therefore also process whereby pressure is modulated without incurring large temperature drops or swings and their associated disadvantages.

This invention provides flexibility in controlling modulation frequency, extraction time as well as extraction efficiency without severely affecting fluid properties. The present invention does not induce large changes in temperature during pressure reduction, and therefore does not cause thermally sensitive material to be damaged.

One aspect of the present invention consists of a practical process for removal of material from the interior of closed or nearly closed matrices such as hard gelatin capsules, vials, bottles, syringes and drums. Under conventional processing conditions, the extraction efficiency from such matrices is often limited by slow diffusion of extracted material through restricted channels or pores of the matrix. In this aspect of the present invention, there is made use of SCFs, in a preferred embodiment $CO_2$, in a novel way to enhance transport of extracted material from inside such matrices to a bulk supercritical phase. Advantages of using non-toxic SCFs such as $CO_2$ in place of organic solvents include environmental friendliness. SCFs such as $CO_2$ further provide high compressibility and diffusivity over a wide range of pressures which allow easy penetration into small interstices and passages with no phase change. Recovery of extracted material from $CO_2$ can also be accomplished by merely expanding it to a low pressure gaseous state and allowing for the condensation or precipitation of extracted material to take place.

In one embodiment of the invention there is disclosed a method for extracting materials from a substrate comprising the steps of: (a) exposing the substrate to a SCF in which said material is substantially soluble but said substrate is not; (b) repeatedly modulating the pressure of said SCF between two or more pressure levels wherein the relative difference between the uppermost and lowermost levels of density during modulation is less than about 30%. Preferably modulation is repeated at least 5 times, more preferably in excess of 20 times, and more preferably in excess of 50 times. More preferably, the difference between the uppermost and lowermost levels of density is less than about 5%.

In another embodiment of the present invention, there is disclosed a method for extracting materials from a substrate such as porous material, microtubing, vials, syringes, bottles and drums comprising the steps of: (a) exposing the substrate to a SCF in which said one or more materials is substantially soluble but said substrate is not; (b) repeatedly modulating the density of said SCF between two or more density levels, wherein the density changes by no more than 30%. Preferably, the relative difference between the uppermost and lowermost levels of density is less than about 5%, and modulation is repeated at least 5 times, more preferably in excess of 20 times, and more preferably in excess of 50 times.

In yet another embodiment of the present invention, there is disclosed a method of treating hard gelatin, cellulose, or plastic capsules used for storing a dry, powdered pharmaceutical formulation wherein the capsule has SCF-soluble material on its internal surfaces comprising the steps of: (a) exposing the capsule to a SCF in which said SCF-soluble material is substantially soluble but in which said capsule is not; (b) repeatedly modulating the pressure of said SCF between two or more pressure levels, wherein the difference between the uppermost and lowermost levels of fluid density is less than about 30%. Preferably the relative difference between the uppermost and lowermost levels of density is less than about 5%, and modulation is repeated at least 5 times, more preferably in excess of 20 times, and more preferably in excess of 50 times.

And yet another embodiment of the present invention entails a method for maintaining the activity of catalysts whose activity can be reduced by transformation products of SCF-soluble by-products of the reaction catalyzed by the catalyst, comprising the steps of: (a) exposing the catalyst to a SCF in which said SCF-soluble product and by-products are substantially soluble but in which said catalyst and its support are not; (b) repeatedly modulating the pressure of said SCF between two or more pressure levels, wherein the relative difference between the uppermost and lowermost levels of density are not more than about 30%. Preferably the relative difference between the uppermost and lowermost levels of density is less than about 5%.

DETAILED DESCRIPTION OF THE INVENTION

The present invention overcomes many of the problems associated with prior art extraction and catalyst activity maintenance schemes. The present invention provides for control of extraction rates, reaction rates, etc., through judicious selection of the magnitude of pressure modulation and the rate of change in pressure. Extraction efficiency can be greater than 7-fold that of conventional SFE.

It has been found that the magnitude of pressure/density modulation, as well as the rate of change in pressure/density, can be used to control the amount of fluid transferred into the bulk phase and the amount of bulk SCF phase forced into the matrix phase. Hold time at the high and/or low pressure/density points can be used where needed to allow adequate time for transfer of extractable material into and out of the matrix fluid phase. Rates of extraction or reaction may be controlled through the selection of suitable magnitude, frequency and hold times for these modulations.

The presently described process promotes the transfer of desirable products of a reaction from catalyst pores to be replaced by bulk supercritical reaction phase during the pressure buildup phase. Such action favors the reaction in the direction that yields the desirable products, and may improve reaction selectivity. Hence, the process can be used advantageously irrespective of whether catalytic reactions produce deactivating material or not.

An embodiment of the present invention further allows for transfer of substances to and from matrices that are normally not efficiently accessed by a fluid thus extending the utility of SFE and reactions in SCFs to applications that were not previously amenable to SCF processing. Application of such embodiment serves to make the use of SCFs even more attractive and thereby increases their potential for use in a variety of processing applications such as extraction of soluble material from capsules, vials, syringes, closed vessels, etc.

The disclosed process of the present invention may find use and be conducted at near-critical and supercritical conditions where the temperature is in the range of about 0.8 to about 2 $T_c$ (where $T_c$ is the critical temperature in K of the fluid), and the pressure is in the range of about 0.5 to about 30 $P_c$ (where $P_c$ is the critical pressure of the fluid). Preferably, the extraction is conducted within a temperature range of about 1.0 to about 1.1 $T_c$, and a pressure in the range of about 1 to about 10 $P_c$. In the case of extraction with $CO_2$, conditions of about 31 to 80° C. and 74 to 700 bar are preferred. The processes may be practiced either isothermally or not. Typically, the lower pressure level should not impart a density to the SCF that is more than about 30% lower than that of the fluid at the higher pressure level. More preferably, the relative difference between the upper level density and the lower level density should be no more than 5%.

The number of pressure/density modulations employed in the described processes generally depends on the specific application. A minimum of two pressure/density modulations is required. The method of control of pressure/density can be either manual or automatic. On/off automatic pressure control is preferred. The pressure profile may resemble either a sinusoidal wave, a square wave, or other profile. Amplitude and frequency of pressure/density modulation may not be constant through a run. The frequency of pressurization and depressurization during any cycle of the described processes also depends on the application. Hold time at the higher and lower pressure/density may change through a process.

Any suitable SCF may be used in the described processes, including, but not limited to, nitrous oxide, sulfur hexafluoride, trifluoromethane, tetrafluromethane, ethane, ethylene, propane, propanol, isopropanol, propylene, butane, butanol, isobutane, isobutene, hexane, cyclohexane, benzene, toluene, o-xylene, ammonia, water, and mixtures thereof. A preferred SCF is $CO_2$. By "supercritical fluid" (SCF) it is meant a substance or a mixture of substances above its critical temperature and critical pressure. The term "supercritical fluid" is also used here to refer to a fluid that has found use at near-critical or supercritical conditions.

The optional composition of a SCF reaction mixture will depend on the specific reactants, products and intermediates. Organic solvent modifiers may also be added to any of the SCFs to modify their solvent properties, including, but not limited to, ethanol, methanol, acetone, propanol, isopropanol, dichloromethane, ethyl acetate, dimethyl sulfoxide, and mixtures thereof. Organic modifiers are used preferably at relatively low concentrations (0–20%). Similarly, light gases such as $N_2$, $O_2$, He, air, $H_2$, $CH_4$ and mixtures thereof may also be added in various proportions to the SCF to alter its extraction or transport properties. Methods for determining these parameters are known to persons of ordinary skill in the art.

This invention addresses a broad spectrum of potential applications in both the pharmaceutical, as well as, the general chemical industry.

In the pharmaceutical and chemical industries, the invention may be used for a variety of applications, including extraction of:

(1) capsule mold lubricant from hard gelatin capsules (e.g., the described method has been shown to reduce drug retention, and reproducibility of drug retention), as well as other material from closed hard shell capsules (including solvents or other soluble material);

(2) material from open, closed or nearly closed pharmaceutical vials (e.g, containers communicating with their environment through relatively restricted channels. Solvents may be extracted from vials containing medication in solution to leave a drug powder—this may be particularly attractive in the case where microdoses of drug cannot be reproducibly metered into a vial in its solid state). Employment of the presently disclosed process is also particularly attractive with respect to high potency drugs which cannot be effectively formulated into tablets or other formulations because of their small mass in the formulation. Small amounts of drug may be metered in the form of a solution into the containers, and the solvent can then be extracted using the disclosed process to leave a residue of virtually pure solid or liquid drug;

(3) soluble materials such as organics from a porous matrix (e.g., the removal may leave a low bioavailability drug finely dispersed in the porous matrix and therefore increase its dissolution rate);

(4) medicinal or chemical substances from natural and synthetic products that are normally not efficiently extracted with SCFs by conventional SFE;

(5) materials from open, closed or nearly closed drums, bottles, syringes, and other containers (extractable material from such containers may include contaminants, solvents, and other hazardous materials such as radioactive and sludge material). The present invention is found to be efficient at extracting material in relatively large quantities and can therefore also be used in applications involving not only extraction of contaminants as in cleaning applications but also extraction of bulk quantities of soluble material. This is demonstrated by the novel application of SCFs to the extraction of bulk material from such substrates as containers, such as bottles, drums and syringes, which are to a large extent impervious to extraction with SCFs at constant pressure and were previously not addressed by other extraction techniques such as pressure pulse and pressure swing. According to this invention, such material is preferably extracted using relatively small modulations in fluid pressure and density. It may be employed to extract a solvent from the internal surface of a container to leave a desirable coating or residue on the internal surface. By incorporating material into the SCF, this method can equally be used to add some desirable substances to the content of the container. If the container has no flow channel though which the SCF can communicate with the contents of the container, and if it is desired that the container not be crushed when exposed to the SCF, one or more small holes may be drilled into the container to allow the SCF to have access to the content without damaging the container. This aspect of the invention is especially attractive for extraction from large containers; and (6) soluble substances from tubing material, especially of the microbore type. All these could have a substantially positive impact on the quality and economics of a product.

The presently disclosed process may also be used to extract material used to facilitate packaging or other operations in the production of content but which, in itself, is not desirable in the final product.

A particularly useful application of the present invention is to alleviate catalyst coking. By periodically and frequently removing a small fraction of the content of the pores (including the small nano-size pores that normally contribute a great deal to the catalyst activity) in a catalyst from the catalyst fluid phase to the bulk fluid phase, the concentration of coking precursors in the catalyst may be maintained at a low enough level that catalyst deactivation is prevented. Alternatively, the presently disclosed process can be used to force one or more reactants into the catalyst pores during pressure buildup, thereby improving reaction rates. Such alternative embodiment may be used, for example, in alkylation procedures which use liquid acid catalysts such as sulfuric acid and hydrofluoric acid (use of a solid catalyst in conjunction with the process provides a means to maintain constant catalytic activity and thereby avoid the use of polluting acid catalysts).

Figure 1:
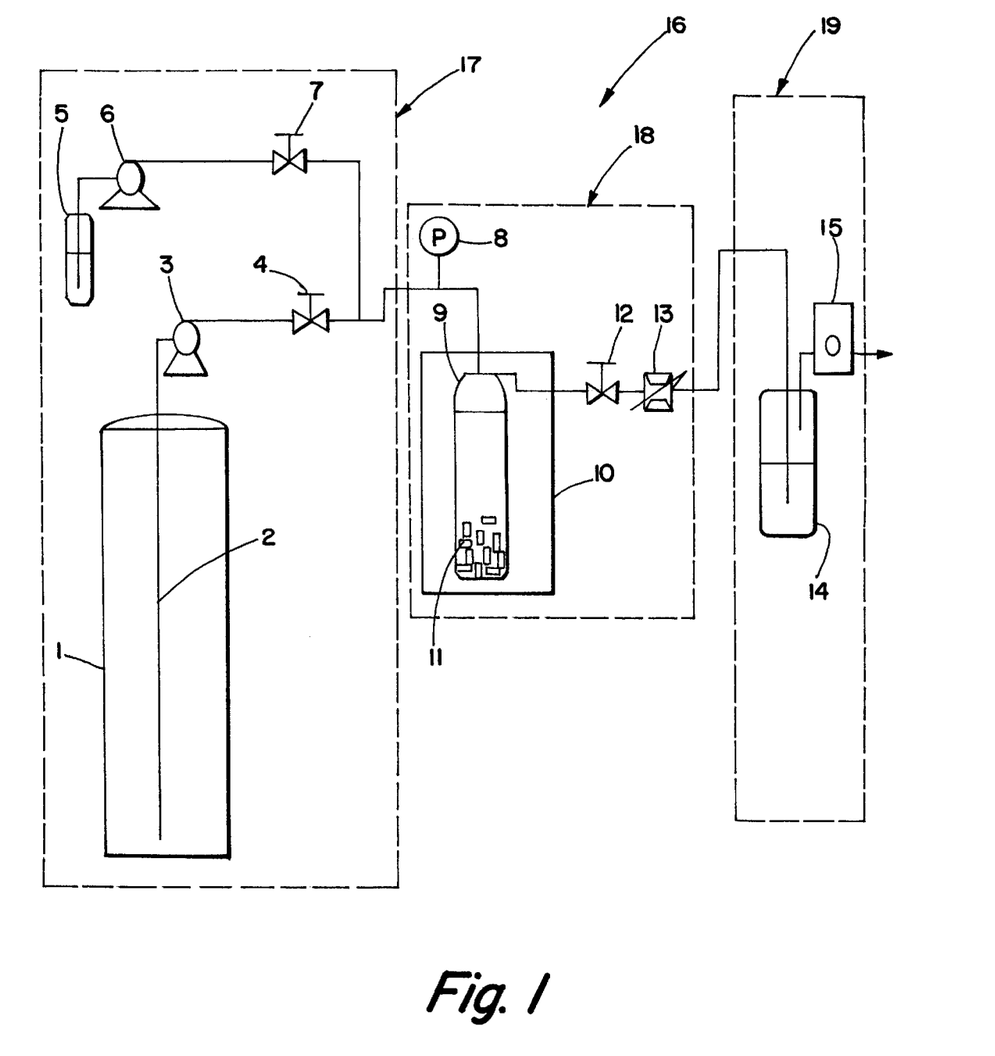
FIG. 1. is a schematic diagram of a conventional supercritical fluid extraction apparatus.

Now turning to the illustrations, there is shown in FIG. 1 a conventional SFE unit generally designated by 16. Unit 16 may be characterized as comprising three main sections: feed section 17, extraction section 18, and extract recovery and flow measurement section 19. In a typical operation, a known amount of material 11 to be extracted is loaded into extraction vessel 9. Extraction vessel 9 is then placed in an isothermal oven 10. Liquid $CO_2$ from $CO_2$ cylinder 1 is subsequently pumped through siphon tube 2 from $CO_2$ cylinder 1 at a constant rate through pump 3 (which is preferably an air-driven pump or a metering pump fitted with a cooled head), and shut-off valve 4. Effluent shutoff valve 12 is initially kept closed until pressure in extraction vessel 9 reaches the desired extraction pressure. Additive may be added to gas entering extraction vessel 9 from additive container 5, by way of pump 6 and valve 7. When the desired pressure is reached, effluent shutoff valve 12 is opened and flow through, heated metering valve 13 and flow meter or totalizer 15 is established. Pressure is then either maintained constant at that pressure level or made to oscillate between two pressure levels continuously with a relatively constant frequency of pressure modulation.

In application of the present invention, pressure/density may be modulated between levels by merely changing inlet air pressure to the pump while keeping effluent $CO_2$ flow rate approximately constant. Pressure modulation may be effected using other ways, including (1) repeatedly reducing pump flow rate while maintaining effluent flow rate relatively constant until pressure reaches the lower level and then increasing pump flow rate to effect a pressure buildup; and (2) repeatedly closing valve 12 to allow for pressure buildup and then opening it to allow for an effluent flow rate that is higher than pump flow rate.

Following expansion through the metering valve 13, $CO_2$ is vented out near atmospheric pressure. The extract may be recovered in vessel 14, for example, by use of a cold trap consisting of a vial immersed in ice or dry ice. At the end of the extraction period, pressure is typically allowed to slowly decrease to atmospheric level. The residue in the vessel is then weighed and prepared for analysis if applicable. As would be recognized by one of ordinary skill in the art, variations in the described experimental procedure are possible, including the possibility of holding the pressure constant for some time prior to reducing pressure, i.e. using a hold time period. $CO_2$ may be vented to higher pressure than atmospheric level and may alternatively be recycled into the process.

SFE units are commercially available from a number of companies including ISCO, Inc. (Lincoln, Nebr.) and Applied Separations (Allentown, Pa.).

Figure 2:
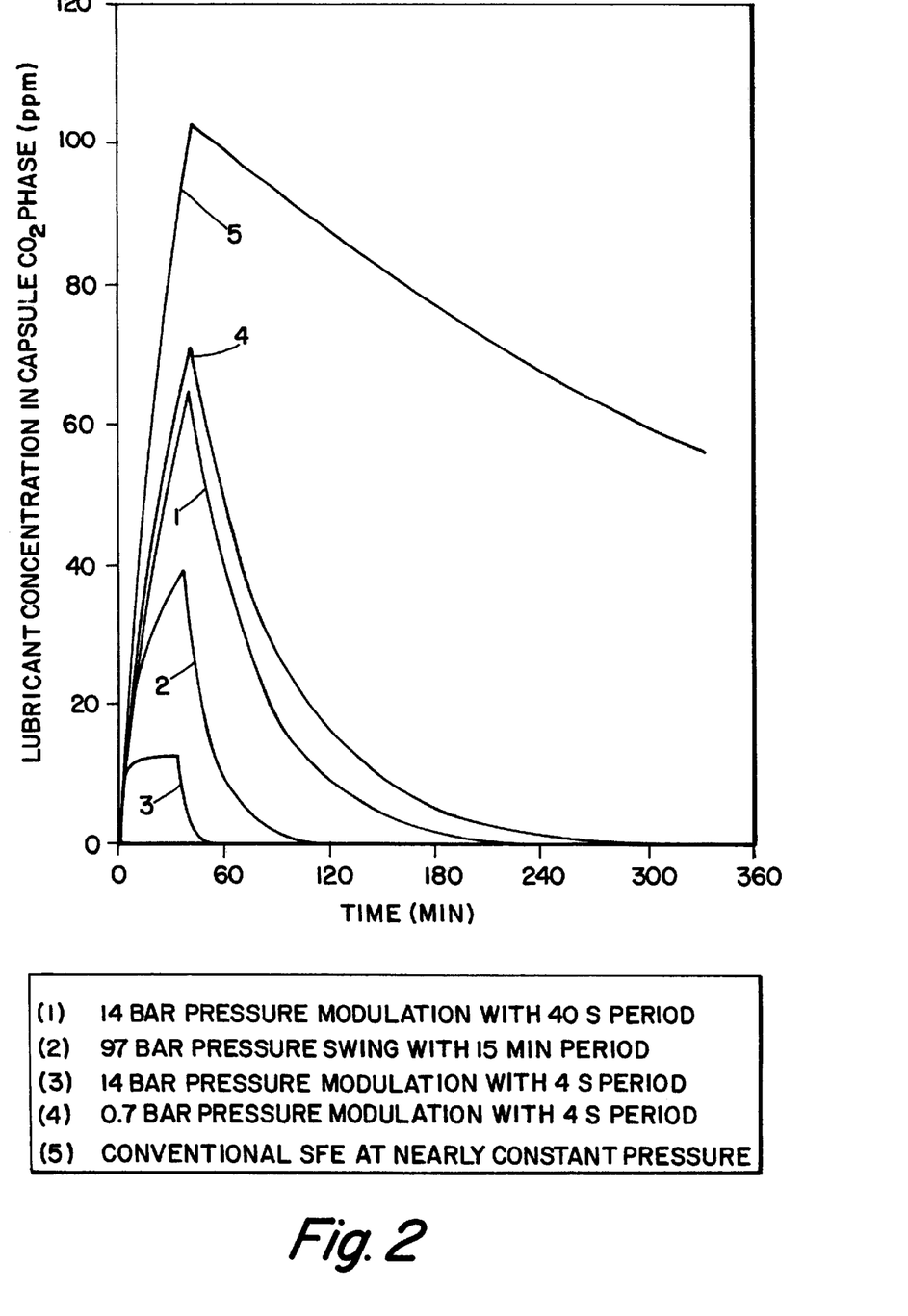
FIG. 2 is a graph of a mathematically predicted evolution of lubricant content in a capsule over time for various pressure fluctuation modes.

Now turning to FIG. 2, there is shown a graph, generated based on a mass transfer model, depicting the predicted evolution of lubricant concentration from conventional assembled gelatin capsules which are placed in supercritical $CO_2$. Five cases were examined where: 25: a nearly constant pressure process where slow and small changes in pressure around 172.4 bar take place (conventional SFE); 24: a nearly constant pressure process where a fluctuation of 0.7 bar takes place in the range of 172.0–172.7 bar with a period of 4 seconds (nearly constant pressure, high frequency); 23: a pressure fluctuation of 14 bar takes place in the range of 165–179 bar with a period of 4 seconds (small pressure modulation, high frequency); 21: a pressure fluctuation of 14 bar takes place in the range of 165–179 bar with a period of 40 seconds (small pressure modulation, low frequency); and 22: a pressure swing or pulse of 97 bar takes place in the range of 172 to 75 bar with a period of 15 minutes. The large period of pressure swing or pulse accounts for the large amount of fluid purged out of the vessel within any period and possibly for the time needed to reheat the vessel to extraction temperature.

Figure 3:
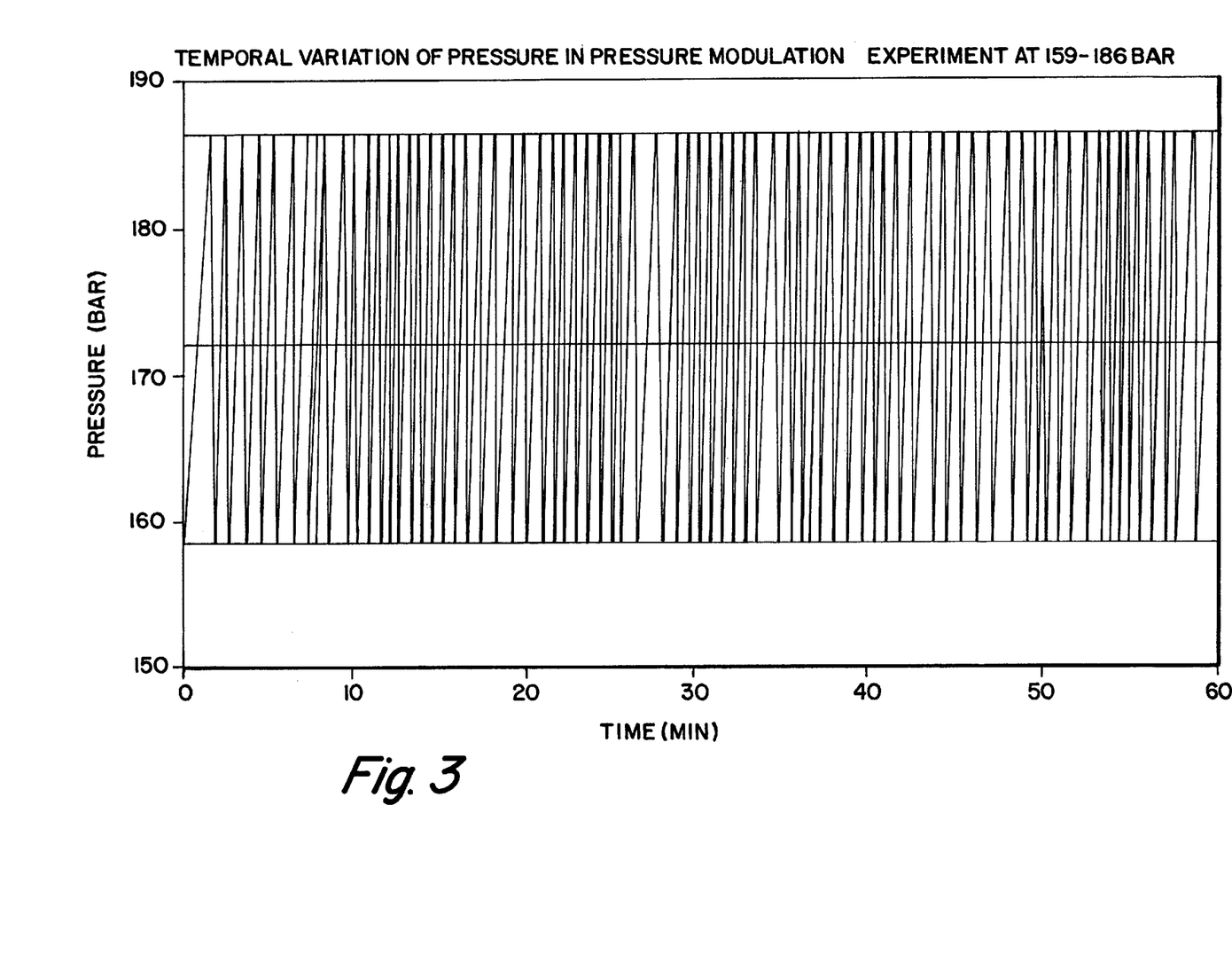
FIG. 3 is a graph of the temporal variation of pressure in a pressure modulation experiment in the pressure range of 159–186 bar.

As shown in FIG. 2 the predicted evolution of the lubricant concentration in the capsule $CO_2$ phase initially increases with time in all cases, presumably because there is a greater rate of extraction of the lubricant from the capsule surface than discharge out of the capsule. In all cases, the capsule surface is completely alleviated of its soluble lubricant fraction after about 45 minutes. FIG. 3 illustrates that the model predicts that both the magnitude of pressure modulation as well as the frequency of modulation are important. The least effective process at removing lubricant from the capsules is the conventional one (25—nearly constant pressure), while the most effective process tested was 23 where a pressure modulation of 14 bar, corresponding to a relative difference in density between the upper level and the lower level of 1.6%, and a short, 4 second period of modulation, are used (relatively small pressure change, high frequency). A pressure swing process with a pressure swing of 97 bars, corresponding to a relative difference in density of 66%, with a 15 minute period was also seen to be more effective than conventional process 25. Minimal changes in pressure of 0.7 bar, corresponding to relative changes in density of about 0.1%, coupled with a short period of fluctuation (4 seconds) can yield a significantly higher extraction efficiency than conventional process 25. Under the conditions of 23, the maximum concentration of lubricant in the capsule $CO_2$ phase was calculated to be only 12 ppm, and the capsule was calculated to be completely purged of its extractable lubricant content after 50 minutes. This compares to 105 minutes for 22, 225 minutes for 21, 285 minutes for 24, and about 800 minutes for 25. Hence, relatively small pressure fluctuations (14 bar), and therefore relatively small density fluctuations, were found to achieve greater extraction efficiencies than larger pressure drops, without the undesirable effects of large pressure drops.

In order to validate the mass transfer model and the presently disclosed process, several experiments were undertaken.

EXAMPLE 1

Temporal Variation of Pressure in Pressure Modulation

FIG. 3 shows a typical example of temporal variation of pressure in pressure modulation in the range of 159–186 bar where no hold time is used at the high pressure end or low pressure end. $CO_2$ density is within the range of 0.8270–0.8553 g/mL. In this experiment, 77 periods of pressure modulation were effected in 1 hour, yielding an average period of modulation of 47 seconds.

EXAMPLE 2

Supercritical Fluid Extraction of Lubricant from Gelatin Capsules: Low Pressure Modulation v. Constant Pressure Lubricant was extracted from gelatin capsules either at constant pressure or using the pressure modulation process. Capsules were placed in a 100 ml beaker and then inserted into a 1 L high pressure vessel. Carbon dioxide flow was directed from the bottom of the vessel to the top of the vessel. Six capsules were used for each test run. Unfilled assembled capsules were treated to remove the lubricant with SCF at either a constant pressure at 172 bar or with the pressure being modulated in the range of 162–183 bar, at a temperature of 35° C. A two hour dynamic extraction time was employed with a $CO_2$ flow rate of about 5 standard liters per minute (SLM). Effluent flow rate out of the vessel is slightly higher or slightly lower than 5 SLM depending on whether pressure is higher or lower than 172 bar respectively. No hold time was used. The capsules were then filled with a powder containing a mixture of ipratropium bromide monohydrate and α-lactose monohydrate. The powder in the capsule was slightly shaken to emulate the tumbling the capsules are subjected to from the time they are manufactured to the time they reach the patient. This shaking serves to contact the powder with the inside surface of the capsules.

Mean retention of the drug in each batch of capsules following simulated inhalation cycles was determined. Table 1 shows the results.

TABLE 1

Supercritical Fluid Extraction of Mold Release Lubricant From Assembled Hard Gelatin Capsules

| TEST RUN | TREATMENT | Δρ (%)* | DRUG RETENTION IN CAPSULE AFTER SIMULATED INHALATION (μg) | STANDARD DEVIATION (μg) |
|---|---|---|---|---|
| 1 | None | N/A | 5.0 | 0.8 |
| 2 | constant Pressure | 0 | 4.4 | 1.2 |
| 3 | Pressure modulation | 2.5 | 4.0 | 0.6 |

*level of fluctuation in supercritical fluid density at pressures employed.

$$\% \Delta\rho = \left(\frac{\rho_{high} - \rho_{low}}{\rho_{high}}\right) * 100 = \left(\frac{\rho_{183} - \rho_{162}}{\rho_{183}}\right) * 100.$$

The results of Table 1 clearly indicate that SFE treated capsules using the low pressure modulation technique retain less ipratropium bromide monohydrate than either unextracted capsules or SFE-treated capsules at constant pressure. The Standard deviation for drug retention was also found to be lower for the capsules extracted by the pressure modulation process. Hence, the pressure/density modulation process is more efficient than the constant pressure process at extracting lubricant from capsules.

EXAMPLE 3

Extraction of Highly Retentive Material from Hard Gelatin Capsules: Low Pressure Modulation v. Constant Pressure In this study, a capsule lot that has been shown to retain large amounts of drug material in simulated inhalation cycles is used. These capsules contain a highly retentive plasticizer material in addition to the mold lubricant on their internal walls and exhibit highly variable retention. Capsules were extracted in their assembled state, i.e. with capsule cap mated to capsule body.

A known amount of capsules was first poured into a 30 mL vessel . The capsules were then extracted at 65° C. for 2 hours using a $CO_2$ flow rate of about 5 SLM at either a constant pressure of 552 bar or by modulation of pressure in the range of 483–621 corresponding to $$\% \Delta\rho = \left(\frac{\rho_{621} - \rho_{483}}{\rho_{621}}\right) * 100 = 5.1\%,$$

where Δρ is the relative difference between the uppermost density and the lowermost density. The period of pressure modulation was about 45 seconds. $CO_2$ was flown through the bottom of the vessel and contacted the capsules directly.

Extracted and untreated capsules were filled with approximately 5 mg of previously described ipratropium bromide-lactose drug powder. The cap was then mated to the body of the filled capsule. After slightly shaking a capsule, it was opened and its content was discharged by holding the capsule cap and body open-ends-down between two fingers on the right hand and the left hand respectively, and vigorously tapping the edge of a container with the upper side of the palms of the hands 4 times to discharge the drug mixture. The mass of the powder after tapping was then determined. Comparison with its mass before tapping provides the mass of retained powder. This test has been shown to provide a good indication of the level of retention that the capsules would exhibit in simulated inhalation cycles.

Five (5) capsules were used in each test. Table 2 shows the results of this study. Untreated capsules retain 31.3% of the drug powder. SFE-treated capsules at constant pressure retain 29.7% of the drug powder. SFE-treated capsules using the pressure modulation technique retain 12.4% of the drug powder. This demonstrates that extraction at constant pressure is not effective at removing any significant amount of material responsible for drug powder retention from inside the capsules indicating strong mass transfer limitations of extractable material from inside the capsules to the bulk $CO_2$ phase outside the capsules. These results also demonstrate that the pressure modulation technique overcomes such limitations and is much more effective at removing such material from the capsules than the conventional process at constant pressure. More importantly, the standard deviation in capsule to capsule retention is much lower for the capsules extracted using the pressure modulation technique than for untreated capsules or capsules extracted at constant pressure. The pressure modulation process brings all capsules to a similar state of low retention.

TABLE 2

Drug Powder Retention in Untreated Capsules, SFE-Treated Capsules by
Conventional SFE and SFE-Treated Capsules by Pressure Modulation

|  | capsule 1 | capsule 2 | capsule 3 | capsule 4 | capsule 5 | Mean | Standard deviation | Range |
|---|---|---|---|---|---|---|---|---|
| *Untreated Capsules* | | | | | | | | |
| Mass of powder blend in filled capsule (g) | 0.0049 | 0.0048 | 0.0051 | 0.0054 | 0.0050 | | | |
| Mass of powder blend in emptied capsule (g) | 0.0017 | 0.0023 | 0.0012 | 0.0011 | 0.0015 | | | |
| mass difference (g) | 0.0032 | 0.0025 | 0.0039 | 0.0043 | 0.0035 | | | |
| % Powder blend Removed | 65.3 | 52.1 | 76.5 | 79.6 | 70.0 | | | |
| % Powder blend retained | 34.7 | 47.9 | 23.5 | 20.4 | 30.0 | 31.3 | 10.8 | 27.5 |
| *Capsules Treated at Constant Pressure* | | | | | | | | |
| Mass of powder blend in filled capsule (g) | 0.0050 | 0.0049 | 0.0051 | 0.0053 | 0.0050 | | | |
| Mass of powder blend in emptied capsule (g) | 0.0011 | 0.0013 | 0.0019 | 0.0013 | 0.0019 | | | |
| weight loss (g) | 0.0039 | 0.0036 | 0.0032 | 0.0040 | 0.0031 | | | |
| % Powder blend Loss Removed | 78.0 | 73.5 | 62.7 | 75.5 | 62.0 | | | |
| % Powder blend retained | 22.0 | 26.5 | 37.2 | 24.5 | 38.0 | 29.7 | 7.4 | 16.0 |
| *Capsules Treated by Pressure Modulation* | | | | | | | | |
| Mass of powder blend in filled capsule (g) | 0.0054 | 0.0053 | 0.0050 | 0.0051 | 0.0051 | | | |
| Mass of powder blend in emptied capsule (g) | 0.0005 | 0.0007 | 0.0008 | 0.0005 | 0.0007 | | | |
| weight loss (g) | 0.0049 | 0.0046 | 0.0042 | 0.0046 | 0.0044 | | | |
| % Powder blend Loss | 90.7 | 86.8 | 84.0 | 90.2 | 86.3 | | | |
| % Powder blend retained | 9.3 | 13.2 | 16.0 | 9.8 | 13.7 | 12.4 | 2.8 | 6.7 |

EXAMPLE 4

Conventional v. Small Pressure Modulation Supercritical Fluid Extraction of Bulk Quantities of a Soluble Material from Assembled Hard Gelatin Capsules In order to further demonstrate that lubricant is actually extracted from the capsules, lubricant material was added to a hard gelatin capsule, and the capsule body was then mated to the capsule cap. This lubricant is partially soluble in $CO_2$ (extractable fraction is 73.3% of mass of lubricant). The pre-closed capsule was then inserted into a 1.62 "long, ¼" I.D., 1.3 mL glass vial. The open vial was then charged into a 32 ml high pressure vessel and $CO_2$ was pumped from the bottom through the top of the vessel.

The capsules were extracted at a constant pressure of 172 bar or pressure was modulated in the range of 165–179 bar for 2 hours at T=35° C. and a $CO_2$ flow rate of about 5 SLM. Extraction efficiency was calculated from the difference in mass between the capsule before extraction and the capsule after extraction. Table 3 shows that a small pressure modulation of 14 bar, equivalent to a density modulation of %Δρ=1.6%, is sufficient to achieve much greater extraction efficiency than conventional SFE.

TABLE 3

Supercritical Fluid Extraction of Bulk Amounts of Lubricant From Pre-Closed Hard Gelatin Capsules - Conventional v. Small Pressure Modulation

| RUN | MASS OF LUBRICANT BEFORE EXTRACTION (mg) | ΔP (bar) | Δρ* (± %) | PERIOD OF PRESSURE MODULATION (seconds) | MASS OF RESIDUAL LUBRICANT (mg) | FRACTIONAL AMOUNT OF LUBRICANT EXTRACTED (%) | SOLUBLE FRACTION OF LUBRICANT REMOVED (%) |
|---|---|---|---|---|---|---|---|
| 1 | 56.2 | 0 | 0 | N/A | 52.4 | 6.8 | 9.3 |
| 2 | 56.1 | 14 | 1.6 | 8 | 39.2 | 30.1 | 41.1 |

For the same amount of $CO_2$, the small pressure modulation technique allows for extraction of more than 4 times more lubricant than conventional SFE. The small amount of lubricant extracted by conventional SFE indicates strong diffusion limitations. The much larger amount extracted by the pressure/density modulation technique indicates that diffusion limitations are overcome.

EXAMPLE 5

Supercritical Fluid Extraction of Lubricant in Capped Glass Vial

This example serves to demonstrate that the present invention can be used to extract material from confined spaces such as vials, bottles, jars, flasks, cylinders, syringes, needles, boxes, tubes, drums, bags, valves, and other substrates whereby access to a relatively large volume of the substrate is restricted, and where pressure modulation could increase the efficiency of extraction.

A known amount of lubricant material was poured into a 1.62 inch long, ¼" I.D., 1.3 mL capped glass vial. The plastic cap was pierced at its center with a 500 μm needle to provide a restricted channel for $CO_2$ to penetrate into the vial without breaking the vial. Note that depending on the type of vial and cap, even in the absence of a small hole, $CO_2$ may penetrate the inside of the vial without breaking the vial. Lubricant was extracted either at a constant pressure of 172 bar or using the pressure modulation method in the range of 154–190 bar. Temperature was 35° C. and $CO_2$ flow rate was about 5 SLM. Table 4A shows the results of extraction of 0.3 g of lubricant from the vials.

As can be seen in Table 4A, little lubricant was extracted in run 1 where pressure was maintained constant throughout the dynamic extraction period. Nearly 17% was extracted in run 2 where pressure was modulated within 36 bar (154–190 bar), corresponding to a relative difference in density of 4.3% between the highest density and the lowest density. Small changes in density are thus observed to be sufficient to sensibly increase the extraction efficiency, demonstrating that small changes in density coupled with a relatively high frequency of modulation are sufficient to overcome the resistance to mixing between the $CO_2$ phase in the vial and the bulk $CO_2$ phase.

In run 2, a period of pressure modulation of 76 seconds, which includes hold times of 1–2 minutes at the lower and upper pressures, was tested. Such test run was compared to run 3 with a period of pressure modulation of 13 seconds with no hold times at the lower and upper pressures. As can be seen an increase in the frequency of pressure modulation by eliminating the hold times, yielded a slightly higher extraction efficiency (20%).

In order to determine if the size of the lubricant sample in the vial affected the extraction, in yet another experiment, 0.3 g of lubricant was distributed among 4 vials containing 0.12, 0.06, 0.06 and 0.06 g respectively and extracted using the small pressure/density modulation process of the present invention. Pressure was modulated in the range of 157–187 bar. Table 4B shows the results of this experiment.

TABLE 4A

Supercritical Fluid Extraction of Lubricant From Capped Vials - Conventional v. Small Pressure Modulation

| RUN | Δρ (%) | DYNAMIC EXTRACTION TIME (hr) | PERIOD OF PRESSURE MODULATION (seconds) | HOLD TIME AT THE LOWER AND HIGHER PRESSURE LEVEL (yes/no) | TOTAL LUBRICANT EXTRACTED (%) | EXTRACTABLE LUBRICANT REMOVED (%) |
|---|---|---|---|---|---|---|
| 1 | 0 | 2 | N/A | N/A | 3.3 | 4.5 |
| 2 | 4.3 | 4.3 | 76 | YES | 16.6 | 22.6 |
| 3 | 4.3 | 4.3 | 13 | NO | 20.0 | 27.3 |

TABLE 4B

Supercritical Fluid Extraction of Lubricant From Capped Vials - Conventional v. Small Pressure Modulation

| RUN | Δρ* (%) | DYNAMIC EXTRACTION TIME (hr) | PERIOD OF PRESSURE MODULATION (seconds) | HOLD TIME AT THE LOWER AND HIGHER PRESSURE LEVEL (yes/no) | TOTAL LUBRICANT EXTRACTED (%) | EXTRACTABLE LUBRICANT REMOVED (%) |
|---|---|---|---|---|---|---|
| 1 | 3.6 | 6 | 37 | N/A | 66.7 | 91.3 |

*level of fluctuation in supercritical fluid density at pressures employed

Table 4B indicates that nearly all extractable lubricant can be removed if enough time is allowed. Lubricant residue in the 3 vials containing 0.06 g of lubricant prior to their extraction contained a dry residue after their extraction, indicating that the soluble fraction of the lubricant was extracted nearly completely from these vials. Residue in vial 4, which contained 0.12 g of lubricant prior to its extraction was still viscous after extraction, indicating that more time would be needed to complete the extraction. Overall extraction yield for the four vials is 91.3%.

EXAMPLE 6

SFE of a Solvent (ethanol) from Capped Glass Vials

This example also serves to demonstrate that the present invention can be used to extract material from confined spaces such as vials, bottles, jars, flasks, cylinders, syringes, needles, boxes, tubes, drums, bags, valves, and other substrates whereby access to a relatively large volume of the substrate is restricted, and where pressure modulation could increase the efficiency of extraction.

A known amount of ethanol was poured into a 1.3 mL capped vial. The plastic cap is pierced at its center with a 500 $\mu$m needle. The vial is then inserted into a 30 mL stainless steel vessel. The solvent is extracted at 35° C. for 1 hour using a $CO_2$ flow rate of about 2.25 SLM at either a constant pressure of 172 bar or by modulating pressure in the range of P=186–159 bar corresponding to $$\% \Delta \rho = \left(\frac{\rho_{186} - \rho_{159}}{\rho_{159}}\right) * 100 = 3.3\%.$$

Table 5 gives the results of the extraction. The results indicate that the pressure modulation process is about 5 times more efficient than conventional SFE at extracting the solvent.

TABLE 5

SFE of Ethanol from a Capped Vial

| Mass of ethanol (g) | 0.78 | 0.79 |
|---|---|---|
| SFE method of extraction | conventional | pressure modulation |
| $\Delta \rho(\%)$ | 0 | 3.3 |
| Period of modulation (s) | Not Applicable | 58 |
| Mass of solvent extracted (g) | 0.14 | 0.71 |
| % solvent extracted | 17.9 | 89.9 |

EXAMPLE 7

SFE of Ethanol from Hydromatrix in Capped Vial

This example serves to demonstrate that the present invention can be used to extract soluble material from porous material such as adsorbent powders and catalysts. In this study, ethanol is extracted from a $CO_2$-insoluble powder matrix. Hydromatrix, also known as diatomaceous earth, was charged into a 1.3 mL. Ethanol was then added to the hydromatrix. The hydromatrix absorbed most of the ethanol. The mixture was then loaded into a capped, 1.3 mL vial. The cap was pierced with a 500 $\mu$m needle. The vial was then inserted into a 30 mL stainless steel vessel. The solvent was extracted at 35° C. using a $CO_2$ flow rate of about 2.75 SLM at either a constant pressure of 103 bar for 1 hour or by modulating pressure in the range of P=90–117 bar corresponding to $$\% \Delta \rho = \left(\frac{\rho_{117} - \rho_{90}}{\rho_{117}}\right) * 100 = 12.9\%$$

for 45 minutes.

Table 6 gives the results of the extraction. Despite the shorter extraction time, the pressure modulation process is still about 5 times more efficient at extracting the solvent than the conventional SFE process.

TABLE 6

SFE of Ethanol from Hydromatrix in a Capped Vial

| Mass of hydromatrix (mg) | 150.0 | 150.0 |
|---|---|---|
| Mass of ethanol + hydromatrix (mg) | 624.7 | 621.2 |
| Mass of ethanol (mg) | 474.7 | 471.2 |
| SFE method of extraction | conventional | pressure modulation |
| $\Delta \rho(\%)$ | 0 | 12.9 |
| Period of modulation (s) | Not Applicable | 90 |
| Mass of solvent extracted (mg) | 3.5 | 17.7 |

EXAMPLE 8

SFE of a Polymeric Material from a Capped Vial

This example serves to demonstrate that the pressure modulation process can be used to extract polymeric material from confined spaces. A small amount of polyethylene glycol (PEG) with an average molecular weight of 200 was pipetted into a 1-mL capped vial. The cap was pierced with a 500 $\mu$m needle. The level of the polymer was about ¼" above the bottom of the vial The polymer was then extracted at either a constant pressure of 165 bar or using the pressure modulation technique in the range of 159–172 bar corresponding to $$\% \Delta \rho = \left(\frac{\rho_{172} - \rho_{159}}{\rho_{172}}\right) * 100 = 1.8\%.$$

Temperature and extraction time were 35° C. and 58 minutes respectively in both runs.

Table 7 shows the result of this study. Despite small pressure and density modulation, the modulation technique is substantially more efficient at removing PEG 200 from the capped vial than conventional SFE. Extraction efficiency is nearly 7-fold higher than that of conventional SFE. The ability to rapidly modulate pressure appears to allow for very high extraction efficiency when compared to conventional SFE.

TABLE 7

SFE of PEG 200 from a Capped Vial

| Mass of PEG 200 (mg) | 119.4 | 111.7 |
|---|---|---|
| SFE method of extraction | conventional | pressure modulation |
| $\Delta \rho(\%)$ | 0 | 1.8 |
| Period of modulation (s) | Not Applicable | 8 |
| Mass of PEG 200 extracted (mg) | 1.0 | 7.7 |

EXAMPLE 9

Effect of Large Drops in Temperature on Capsule Integrity

Approximately 100,000 hard gelatin capsules held in seven cotton bags were charged successively into an eighty liter cylindrical stainless steel vessel. The objective was to extract the capsules with supercritical $CO_2$ by modulating pressure in the range of 172–103 bar. Preheated $CO_2$ was pumped into the vessel through the top of the vessel. Pressure reduction was conducted by periodically purging $CO_2$ from the bottom of the vessel. Inadequate control of pressure and inability to efficiently reheat the vessel following a pressure drop caused the pressure to drop below 103 bar and temperature at the bottom of the vessel, near the expansion valve, to decrease substantially to near freezing range. A large fraction of the capsules at the bottom of the vessel, near the location of the valve through which expansion of $CO_2$ was effected, were shattered or were otherwise damaged. Nearly 61% of the capsules placed into the three lower bags were damaged. Only 17% of the capsules in the four upper bags were damaged. Inability to control temperature at one location of the vessel was thus seen to cause extensive damage to the thermally sensitive capsules.

While the invention has been described with respect to preferred embodiments, those skilled in the art will readily appreciate that various changes and/or modifications can be made to the invention without departing from the spirit or scope of the invention as defined by the appended claims.

What is claimed is:

1. A method for extracting supercritical fluid soluble material from one or more cavities or confined spaces in a substrate comprising the steps of:
    a) exposing the substrate to a supercritical fluid in which said material is substantially soluble but said substrate is not, wherein said supercritical fluid has a critical temperature less than about 200° C. and a critical pressure of less than about 10,000 psi and wherein said substrate is a container selected from the group consisting of vials, bottles, jars, flasks, cylinders, capsules, boxes, tubes, drums and bags; and
    b) repeatedly modulating the pressure of said supercritical fluid between two or more pressure levels such that the relative difference between the uppermost and lowermost levels of density of said supercritical fluid at such pressure levels is not more than about 30%.

2. The method of claim 1 wherein said method is conducted at near-critical or supercritical conditions.

3. The method of claim 1 wherein said method is conducted at a temperature in the range of about 0.8 to about 2 times the critical temperature of the fluid in degrees Kelvin.

4. The method of claim 1 wherein the uppermost pressure level of said two or more pressure levels is within the range of about 0.5 to about 30 times the critical pressure of the supercritical fluid.

5. The method of claim 1 wherein the uppermost pressure level of said two or more pressure levels is within the range of about 1 to about 10 times the critical pressure of the supercritical fluid.

6. The method of claim 1 wherein said method is conducted at a temperature in the range of about 1 to about 1.1 times the critical temperature of the fluid in degrees Kelvin.

7. The method of claim 1 wherein said supercritical fluid is maintained at conditions such that the relative difference between the density level achieved at the uppermost pressure level and the lowermost pressure level of said two or more pressure levels is no more than about 5%.

8. The method of claim 1 wherein said pressure modulation is repeated multiple times.

9. The method of claim 1 wherein said pressure modulation is repeated at least 5 times.

10. The method of claim 1 wherein said pressure modulation is repeated at least 20 times.

11. The method of claim 1 wherein said pressure modulation is repeated at least 50 times.

12. The method of claim 1 wherein said pressure modulation is repeated until more than 50% of the material is removed from said substrate.

13. The method of claim 1 wherein said pressure modulation is repeated until more than 75% of the material is removed from said substrate.

14. The method according to claim 1 wherein the supercritical fluid is or comprises carbon dioxide.

15. The method according to claim 1 wherein said substrate is sensitive to large changes in pressure, temperature or density.

16. A method for treating gelatin, cellulose, modified starch, or plastic capsules used for storing a dry, powdered formulation wherein the capsule has supercritical fluid-extractable material on its surfaces comprising the steps of:
    a) exposing the capsule to a supercritical fluid in which said supercritical fluid-extractable material is substantially extractable but in which said capsule is not, wherein said supercritical fluid has a critical temperature less than about 200° C. and a critical pressure of less than about 10,000 psi; and
    b) repeatedly modulating the pressure of said supercritical fluid between two or more pressure levels such that the relative difference between the uppermost and lowermost levels of density of said supercritical fluid at such pressure levels is not more than about 30%.

17. The method according to claim 16 wherein said supercritical fluid-extractable material is capsule mold lubricant.

18. The method according to claim 16 wherein said supercritical fluid-extractable material is capsule plasticizing material.

19. The method according to claim 16 wherein said capsule comprises a capsule body and a capsule cap, said capsule cap dimensioned so as to snuggly fit on said capsule body such that when said capsule cap is assembled on said capsule body, a surface of said capsule cap and capsule body define an enclosed void.

20. The method according to claim 19 wherein said capsule is exposed to said supercritical fluid in an assembled state.

21. The method according to claim 19 wherein said enclosed void of said capsule contains a pharmaceutical or nutritional material.

22. The method according to claim 21 wherein said pharmaceutical material comprises ipratropium bromide.

23. The method according to claim 19 wherein said capsule is exposed to said supercritical fluid in a disassembled state.

24. A capsule treated by the method of claim 16.

25. The method according to claim 1 wherein the one or more cavities in said substrate are closed or nearly closed.

26. A method as in claim 16 wherein said modified starch is modified cellular starch.

* * * * *